(12) United States Patent
Steigerwald et al.

(10) Patent No.: US 8,772,023 B2
(45) Date of Patent: Jul. 8, 2014

(54) PROMOTERS FOR RECOMBINANT VIRAL EXPRESSION

(75) Inventors: Robin Steigerwald, Munich (DE); Christine Meisinger-Henschel, Neuried (DE); Eva Felder, Munich (DE)

(73) Assignee: Bavarian Nordic A/S, Kvistgaard (DK)

( * ) Notice: Subject to any disclaimer, the term of this patent is extended or adjusted under 35 U.S.C. 154(b) by 30 days.

(21) Appl. No.: 13/131,586

(22) PCT Filed: Nov. 27, 2009

(86) PCT No.: PCT/EP2009/008459
§ 371 (c)(1),
(2), (4) Date: Sep. 19, 2011

(87) PCT Pub. No.: WO2010/060632
PCT Pub. Date: Jun. 3, 2010

(65) Prior Publication Data
US 2012/0121617 A1    May 17, 2012

(30) Foreign Application Priority Data
Nov. 27, 2008   (EP) .................................... 08020617

(51) Int. Cl.
C12N 15/00    (2006.01)
A61K 39/12    (2006.01)

(52) U.S. Cl.
USPC .................................... 435/320.1; 424/199.1

(58) Field of Classification Search
None
See application file for complete search history.

(56) References Cited

FOREIGN PATENT DOCUMENTS

EP    1 536 015 A1    6/2005

OTHER PUBLICATIONS

Saito et al. The Interaction of Akt with APPL1 is Required for Insulin-stimulated Glut4 Translocation. Nov. 2, 2007. The Journal of Biological Chemistry. vol. 282, No. 44, p. 32280-32287.*
Beilharz et al. Widespread use of poly(A) tail length control to accentuate expression of the yeast transcriptome. 2007. RNA. vol. 13, pp. 982-997.*
Ng et al. A physical map of the genome of Atlantic salmon, *Salmo salar*. 2005. Genomics. vol. 86, pp. 396-404.*
Sequence Alignment of SEQ ID No. 2 with Accession ET418770, Nov. 12, 2013; 1 page.*
A.J. Davison et al., "Structure of Vaccinia Virus Late Promoters," *J. Mol. Biol.* 210(4):771-784 (1989).
Y. Li et al., "High-level expression of *Amsacta moorei* entomopoxvirus *spheroidin* depends on sequences within the gene," *J. Gen. Virol.* 79(3):613-622 (1998).
G. Sutter et al., "A recombinant vector derived from the host range-restricted and highly attenuated MVA strain of vaccinia virus stimulates protective immunity in mice to influenza virus," *Vaccine* 23(11):1032-1040 (1994).
EMBL Database Accession No. C11445, entry created Sep. 14, 1996.
EMBL Database Accession No. FH681342, entry created Jun. 24, 2008.
EMBL Database Accession No. AQ611252, entry created Jun. 24, 1999.
EMBL Database Accession No. BB450912, entry created Jul. 12, 2000.
EMBL Database Accession No. EV481527, entry created Oct. 29, 2007.
EMBL Database Accession No. BV874789, entry created Oct. 8, 2008.
EMBL Geneseq Accession No. AFT30885, entry created Feb. 7, 2008.
Extended European Search Report for EP 08020617.0, issued Apr. 1, 2009.
International Search Report and Written Opinion of the International Searching Authority for International Application No. PCT/EP2009/008459, issued Jan. 26, 2010.

* cited by examiner

*Primary Examiner* — Anne Gussow
*Assistant Examiner* — Channing S Mahatan
(74) *Attorney, Agent, or Firm* — Law Office of Salvatore Arrigo and Scott Lee, LLP

(57) ABSTRACT

The invention relates to a promoter selected from a group of nucleic acids consisting of (a) a nucleic acid having the nucleotide sequence of SEQ ID NO:1; (b) a nucleic acid having a nucleotide sequence derived from SEQ ID NO:1, wherein not more than 10 nucleotides have been added, deleted, substituted and/or inverted from the nucleic acid of SEQ ID NO:1; and (c) a nucleic acid sequence having at least 70% identity with the nucleic acid of (a); wherein the promoter has a length of up to and including 27 nucleotides and wherein the promoter according to options (b) and (c) exhibits at least the 70% of the promoter activity of SEQ ID NO:1 as measured by the amount of recombinant protein produced.

24 Claims, 3 Drawing Sheets

SEQUENCE LISTING

<160> NUMBER OF SEQ ID NOS: 34

<210> SEQ ID NO 1
<211> LENGTH: 16
<212> TYPE: DNA
<213> ORGANISM: Artificial Sequence
<220> FEATURE:
<223> OTHER INFORMATION: synthetic sequence

<400> SEQUENCE: 1 aattttaat atataa                                                    16

<210> SEQ ID NO 2
<211> LENGTH: 20
<212> TYPE: DNA
<213> ORGANISM: Artificial Sequence
<220> FEATURE:
<223> OTHER INFORMATION: synthetic sequence

<400> SEQUENCE: 2 aattttaat atataaatgg                                                20

<210> SEQ ID NO 3
<211> LENGTH: 19
<212> TYPE: DNA
<213> ORGANISM: Artificial Sequence
<220> FEATURE:
<223> OTHER INFORMATION: synthetic sequence

<400> SEQUENCE: 3 aattttaat atataaatg                                                 19

<210> SEQ ID NO 4
<211> LENGTH: 18
<212> TYPE: DNA
<213> ORGANISM: Artificial Sequence
<220> FEATURE:
<223> OTHER INFORMATION: synthetic sequence

<400> SEQUENCE: 4 aattttaat atataaat                                                  18

<210> SEQ ID NO 5
<211> LENGTH: 19
<212> TYPE: DNA
<213> ORGANISM: Artificial Sequence
<220> FEATURE:
<223> OTHER INFORMATION: synthetic sequence

<400> SEQUENCE: 5 aattttaat atataaata                                                 19

<210> SEQ ID NO 6
<211> LENGTH: 13
<212> TYPE: DNA
<213> ORGANISM: Artificial Sequence
<220> FEATURE:
<223> OTHER INFORMATION: synthetic "filler" sequence

<400> SEQUENCE: 6
ttcagtccta tgg                                                      13

<210> SEQ ID NO 7
<211> LENGTH: 20
<212> TYPE: DNA
<213> ORGANISM: Artificial Sequence -continued
<220> FEATURE:
<223> OTHER INFORMATION: part of 128L gene of modified vaccinia virus Ankara (MVA)

<400> SEQUENCE: 7 atttttaat atataaatga 20

<210> SEQ ID NO 8
<211> LENGTH: 20
<212> TYPE: DNA
<213> ORGANISM: Artificial Sequence
<220> FEATURE:
<223> OTHER INFORMATION: part of LC16m8 gene of vaccinia virus

<400> SEQUENCE: 8
catttttaat atataaatga 20

<210> SEQ ID NO 9
<211> LENGTH: 28
<212> TYPE: DNA
<213> ORGANISM: Artificial Sequence
<220> FEATURE:
<223> OTHER INFORMATION: ORF1

<400> SEQUENCE: 9
tgaaacaata tatcgtactg gcatgcat 28

<210> SEQ ID NO 10
<211> LENGTH: 28
<212> TYPE: DNA
<213> ORGANISM: Artificial Sequence
<220> FEATURE:
<223> OTHER INFORMATION: ORF2

<400> SEQUENCE: 10
ataaacacgg agtttatttt atatgtct 28

<210> SEQ ID NO 11
<211> LENGTH: 28
<212> TYPE: DNA
<213> ORGANISM: Artificial Sequence
<220> FEATURE:
<223> OTHER INFORMATION: ORF3

<400> SEQUENCE: 11
aaaaaatagt tgttaactaa tcatgagg 28

<210> SEQ ID NO 12
<211> LENGTH: 28
<212> TYPE: DNA
<213> ORGANISM: Artificial Sequence
<220> FEATURE:
<223> OTHER INFORMATION: ORF4

<400> SEQUENCE: 12
tattgttatt gttaatttag ttatggaa 28

<210> SEQ ID NO 13
<211> LENGTH: 28
<212> TYPE: DNA
<213> ORGANISM: Artificial Sequence
<220> FEATURE:
<223> OTHER INFORMATION: ORF5

<400> SEQUENCE: 13
acatttatta aaccgcatca agatgggt 28

<210> SEQ ID NO 14
<211> LENGTH: 28
<212> TYPE: DNA
<213> ORGANISM: Artificial Sequence
<220> FEATURE:
<223> OTHER INFORMATION: ORF6

<400> SEQUENCE: 14
ttgttttttt tctatgctat aaatgaat                                              28

<210> SEQ ID NO 15
<211> LENGTH: 28
<212> TYPE: DNA
<213> ORGANISM: Artificial Sequence
<220> FEATURE:
<223> OTHER INFORMATION: ORF7

<400> SEQUENCE: 15
aaaagttgtt tggtgaactt aaatggcg                                              28

<210> SEQ ID NO 16
<211> LENGTH: 28
<212> TYPE: DNA
<213> ORGANISM: Artificial Sequence
<220> FEATURE:
<223> OTHER INFORMATION: ORF8

<400> SEQUENCE: 16
tttaagtttt tgatacccat aaatgaag                                              28

<210> SEQ ID NO 17
<211> LENGTH: 28
<212> TYPE: DNA
<213> ORGANISM: Artificial Sequence
<220> FEATURE:
<223> OTHER INFORMATION: ORF9

<400> SEQUENCE: 17
gatactaatt gtagctattt aaatgggt                                              28

<210> SEQ ID NO 18
<211> LENGTH: 28
<212> TYPE: DNA
<213> ORGANISM: Artificial Sequence
<220> FEATURE:
<223> OTHER INFORMATION: ORF10

<400> SEQUENCE: 18
atcacaaaaa aaacttctct aaatgagt                                              28

<210> SEQ ID NO 19
<211> LENGTH: 28
<212> TYPE: DNA
<213> ORGANISM: Artificial Sequence
<220> FEATURE:
<223> OTHER INFORMATION: ORF11

<400> SEQUENCE: 19
gcaaagcttt tgcgatcaat aaatggat                                              28

<210> SEQ ID NO 20
<211> LENGTH: 28
<212> TYPE: DNA
<213> ORGANISM: Artificial Sequence
<220> FEATURE:

```
<223> OTHER INFORMATION: ORF12

<400> SEQUENCE: 20
tatgattaat ttcaataact aaatggcg                                              28

<210> SEQ ID NO 21
<211> LENGTH: 28
<212> TYPE: DNA
<213> ORGANISM: Artificial Sequence
<220> FEATURE:
<223> OTHER INFORMATION: ORF13

<400> SEQUENCE: 21
cttattatcc ttaactataa aaatgtcc                                              28

<210> SEQ ID NO 22
<211> LENGTH: 28
<212> TYPE: DNA
<213> ORGANISM: Artificial Sequence
<220> FEATURE:
<223> OTHER INFORMATION: ORF14

<400> SEQUENCE: 22 tattttttt atatcgatat tgatggac                                               28

<210> SEQ ID NO 23
<211> LENGTH: 28
<212> TYPE: DNA
<213> ORGANISM: Artificial Sequence
<220> FEATURE:
<223> OTHER INFORMATION: ORF15

<400> SEQUENCE: 23
cagttatcat ttcattttta ctatgccg                                              28

<210> SEQ ID NO 24
<211> LENGTH: 28
<212> TYPE: DNA
<213> ORGANISM: Artificial Sequence
<220> FEATURE:
<223> OTHER INFORMATION: ORF16

<400> SEQUENCE: 24
gtaaaaacta cgaatataaa taatggaa                                              28

<210> SEQ ID NO 25
<211> LENGTH: 28
<212> TYPE: DNA
<213> ORGANISM: Artificial Sequence
<220> FEATURE:
<223> OTHER INFORMATION: ORF17

<400> SEQUENCE: 25
caattcaatt ttaaagcctt aaatggac                                              28

<210> SEQ ID NO 26
<211> LENGTH: 28
<212> TYPE: DNA
<213> ORGANISM: Artificial Sequence
<220> FEATURE:
<223> OTHER INFORMATION: ORF18

<400> SEQUENCE: 26
gtcgtcattt aatactaaat aaatgatg                                              28
```

```
<210> SEQ ID NO 27
<211> LENGTH: 28
<212> TYPE: DNA
<213> ORGANISM: Artificial Sequence
<220> FEATURE:
<223> OTHER INFORMATION: ORF19

<400> SEQUENCE: 27
taaaaatatt tttagcttct aaatggcg                                      28

<210> SEQ ID NO 28
<211> LENGTH: 28
<212> TYPE: DNA
<213> ORGANISM: Artificial Sequence
<220> FEATURE:
<223> OTHER INFORMATION: ORF20

<400> SEQUENCE: 28
atagtgaagt tattgtcaat aaatgatt                                      28

<210> SEQ ID NO 29
<211> LENGTH: 28
<212> TYPE: DNA
<213> ORGANISM: Artificial Sequence
<220> FEATURE:
<223> OTHER INFORMATION: ORF21

<400> SEQUENCE: 29
atttaaaatt tttattagtt aaatggat                                      28

<210> SEQ ID NO 30
<211> LENGTH: 28
<212> TYPE: DNA
<213> ORGANISM: Artificial Sequence
<220> FEATURE:
<223> OTHER INFORMATION: ORF22

<400> SEQUENCE: 30
agtgacattt tttaatatat aaatgagt                                      28

<210> SEQ ID NO 31
<211> LENGTH: 28
<212> TYPE: DNA
<213> ORGANISM: Artificial Sequence
<220> FEATURE:
<223> OTHER INFORMATION: ORF23

<400> SEQUENCE: 31
agtgatgtga caccatcggt ggatgtcg                                      28

<210> SEQ ID NO 32
<211> LENGTH: 28
<212> TYPE: DNA
<213> ORGANISM: Artificial Sequence
<220> FEATURE:
<223> OTHER INFORMATION: ORF24

<400> SEQUENCE: 32
gtttctaaaa tctgtacttt aaatggac                                      28

<210> SEQ ID NO 33
<211> LENGTH: 16
<212> TYPE: DNA
<213> ORGANISM: Artificial sequence
<220> FEATURE:
<223> OTHER INFORMATION: synthetic sequence
```

```
<400> SEQUENCE: 33
aatttttaat ctataa                                                     16

<210> SEQ ID NO 34
<211> LENGTH: 16
<212> TYPE: DNA
<213> ORGANISM: Artificial sequence
<220> FEATURE:
<223> OTHER INFORMATION: synthetic sequence

<400> SEQUENCE: 34
attttttatt ctataa                                                     16
```

PROMOTERS FOR RECOMBINANT VIRAL EXPRESSION

This application is a National Phase application under 35 U.S.C. §371 of International Application No. PCT/EP2009/008459, filed Nov. 27, 2009, and claims the benefit under 35 U.S.C. §365 of European Application No. 08020617.0, filed Nov. 27, 2008, the disclosures of which are incorporated herein by reference in their entirety.

FIELD OF THE INVENTION

The present invention relates to a novel promoter of protein expression of genes in poxviruses, especially in vaccinia viruses such as modified vaccinia virus Ankara (MVA). The invention further relates to polynucleotides comprising said promoter, in particular, polynucleotides comprising said promoter and a nucleic acid to be expressed; vectors comprising the same; host cells comprising the above constructs; and compositions comprising any of the above. The invention further relates to the use of any of the above constructs for expressing a nucleic acid, preferably a gene; the use of the above constructs for preparation of a medicament for treatment and/or prophylaxis of various diseases; a method of treatment and/or prophylaxis of various diseases; a method of preparing a polypeptide, where this method implements the above constructs; and a method of expressing a nucleic acid, where the method implements certain of the above constructs.

BACKGROUND OF THE INVENTION

Recombinant poxviruses are widely used to express foreign antigens in infected cells. Moreover, recombinant poxviruses are very promising vaccines for inducing an immune response against the foreign antigen expressed from the poxvirus vector. Most popular are avipoxviruses on the one hand and, on the other hand, vaccinia viruses, in particular modified vaccinia virus Ankara ("MVA"). MVA is related to vaccinia virus, a member of the genus Orthopoxvirus in the family of Poxyiridae.

MVA has been generated by 516 serial passages on chicken embryo fibroblasts of the Ankara strain of vaccinia virus (CVA) (for review, see Mayr et al. (1975) Infection 3, 6-14). As a consequence of these long-term passages, the resulting MVA virus deleted about 31 kilobases of its genomic sequence and, therefore, was described as highly host cell-restricted to avian cells (Meyer et al. (1991) J. Gen Virol. 72, 1031-1038). It was shown, in a variety of animal models, that the resulting MVA was significantly avirulent (Mayr and Danner (1978) Dev. Biol. Stand. 41, 225-34). Additionally, this MVA strain has been tested in clinical trials as a vaccine to immunize against the human smallpox disease.

For the expression of heterologous genes in pox viruses, only a few promoters are known, such as the 30K and 40K promoters (see for example U.S. Pat. No. 5,747,324), a strong synthetic early/late promoter (see for example Sutter et al. (1994) Vaccine 12, 1032-1040), the Pr7.5 promoter (7.5K promoter; see for example Endo et al. (1991) J. Gen. Virol 72, 699-703) and the promoter derived from the cowpox virus A-type inclusion (ATI) gene (PrATI, Li et al. (1998) J. Gen. Virol. 79, 613). All of these promoters have been used in recombinant vaccinia viruses to express heterologous genes and were shown to express said genes resulting in the production of the protein encoded by the heterologous gene. However, there is still a general need for alternative promoters, specifically strong promoters, in vaccinia viruses.

MVA is thus widely used as a vaccine as well as an expression system to make large amounts of recombinant protein. Especially in its use as vaccine, it is desirable to produce high levels of antigen, as the desired immune response elicited depends in part on the amount of protein produced following administration of the MVA-containing vaccine. Up to now, enhancing the desired immunogenicity of a protein has been accomplished in a number of ways. First, when administering the naked antigenic protein as a vaccine, larger amounts of the relevant protein may be introduced into the subject to be vaccinated. In a vaccine based on a recombinant expression system, i.e. a vaccine in which the encoding nucleic acid is administered, for example, in a poxvirus vector such as MVA, and the actual immune response is elicited by a protein expressed from this nucleic acid, it is also possible to enhance immunogenicity by enhancing the transcription of the antigen (Wyatt et al. (2008) Vaccine 26, 486-493). It is also possible to enhance the translation of already transcribed RNA. Finally, immunogenicity can be enhanced by enhancing the presentation of the antigen to the immune system.

One problem frequently encountered in designing viral recombinant expression systems, especially for use as vaccines, is that the constructs often lack stability at the nucleic acid level. Further, the nucleic acid is frequently subject to undesired recombination within the viral vector, which often reduces, and in some cases even abrogates, the capacity of the viral vector to produce the desired immunogenic peptide in the vaccinated host.

It is therefore an aim to overcome these problems while retaining the high degree of protein expression required for eliciting a sufficient immunogenic response.

SUMMARY OF THE INVENTION

One aspect of the invention provides a promoter selected from the group of nucleic acids consisting of:
(a) a nucleic acid having a nucleotide sequence as set out in SEQ ID NO: 1 ("PrSSL", respectively);
(b) a nucleic acid having a nucleotide sequence derived from the nucleic acid set out in (a), comprising at least one nucleotide addition, deletion, substitution and/or inversion as compared to the nucleotide sequence of (a) and having essentially the same expression characteristics as the nucleic acid of (a);
(c) a nucleic acid sequence having at least 70% identity with the nucleic acid of (a) and having essentially the same expression characteristics as the nucleic acid of (a); and
(d) a nucleic acid capable of hybridizing to a nucleic acid sequence of (a), (b) or (c) and having essentially the same expression characteristics as the nucleic acid of (a).

Preferably, the promoter has a length of up to and including 27 nucleotides.

Preferably the promoter has the nucleotide sequence as set out in SEQ ID NO 33 or 34.

A further aspect of the invention provides a polynucleotide comprising the promoter as set out above. Preferably, the polynucleotide may comprise in addition to the promoter further nucleotides added from position +1.

Preferably, the polynucleotide has the sequence as set out in SEQ ID NO 2, 3, 4 or 5.

A further aspect of the invention provides a polynucleotide comprising a promoter as set out above or a polynucleotide as set out above and a nucleic acid to be expressed.

A further aspect of the invention provides a vector comprising a promoter or a polynucleotide as set out above.

In a further aspect, the invention provides a host cell comprising a promoter as set out above, a polynucleotide as set out above and/or a vector as set out above.

A further aspect of the invention provides a composition comprising a promoter as set out above, a polynucleotide as set out above, a vector as set out above, and/or a host cell as set out above.

In a further aspect, the invention provides a promoter as set out above, a polynucleotide as set out above, a vector as set out above, a host cell as set out above and/or a composition as set out above for use in a vaccine.

A further aspect of the invention provides a use of a promoter as set out above, a polynucleotide as set out above, a vector as set out above, a host cell as set out above and/or a composition as set out above for expressing a nucleic acid, preferably a gene.

A further aspect of the invention provides a promoter as set out above, a polynucleotide as set out above, a vector as set out above, a host cell as set out above and/or a composition as set out above as a pharmaceutical.

A further aspect of the invention provides a use of a promoter as set out above, a polynucleotide as set out above, a vector as set out above, a host cell as set out above and/or a composition as set out above in the preparation of a medicament for inducing an immune response or for the treatment or the prophylaxis of cancer and/or an infectious disease.

A further aspect of the invention provides a promoter as set out above, a polynucleotide as set out above, a vector as set out above, a host cell as set out above and/or a composition as set out above for inducing an immune response or for the treatment or the prophylaxis of cancer and/or an infectious disease.

In a further aspect, the invention provides a method of preparing a polypeptide comprising:
(a) providing a polynucleotide as set out above, wherein the nucleic acid sequence to be expressed comprises an open reading frame ("ORF") or a partial ORF;
(b) subjecting the polynucleotide of (a) to conditions conducive to transcription and translation of the nucleic acid to be expressed;
(c) recovering the polypeptide; and
(d) optionally purifying the polypeptide.

A further aspect of the invention provides a method of expressing a nucleic acid, said method comprising providing a polynucleotide comprising a nucleic acid to be expressed; providing a promoter as set out above or a polynucleotide comprising the promoter, operably linked to the nucleic acid to be expressed; and subjecting the thus provided nucleotide to conditions conducive to the expression of the nucleic acid.

A further aspect of the invention relates to a method for inducing an immune response or a method for the treatment or for the prophylaxis of cancer and/or an infectious disease comprising providing the promoter as set out above, a polynucleotide as set out above, a vector as set out above, a host cell as set out above and/or a composition as set out above and administering the composition to a subject animal, including human.

BRIEF DESCRIPTION OF THE FIGURES

Table 1: Determination of the promoter as given in SEQ ID NO: 1. Alignment of regions surrounding the start codon from 24 MVA genes assumed to yield high levels of expressed protein. The first two lines below the table indicate the most frequent nucleotide at each position in the sequence, and the frequency of this nucleotide. The last two lines below the table indicate the second-most frequent nucleotide at each position in the sequence, and the frequency of this nucleotide. A blank below a column signifies a frequency of less than 25%. Two nucleotides at a given position indicate the identical frequencies for these nucleotides at the given position. Table 1 is included at the end of the Examples.

DETAILED DESCRIPTION OF THE INVENTION

Figure 1:
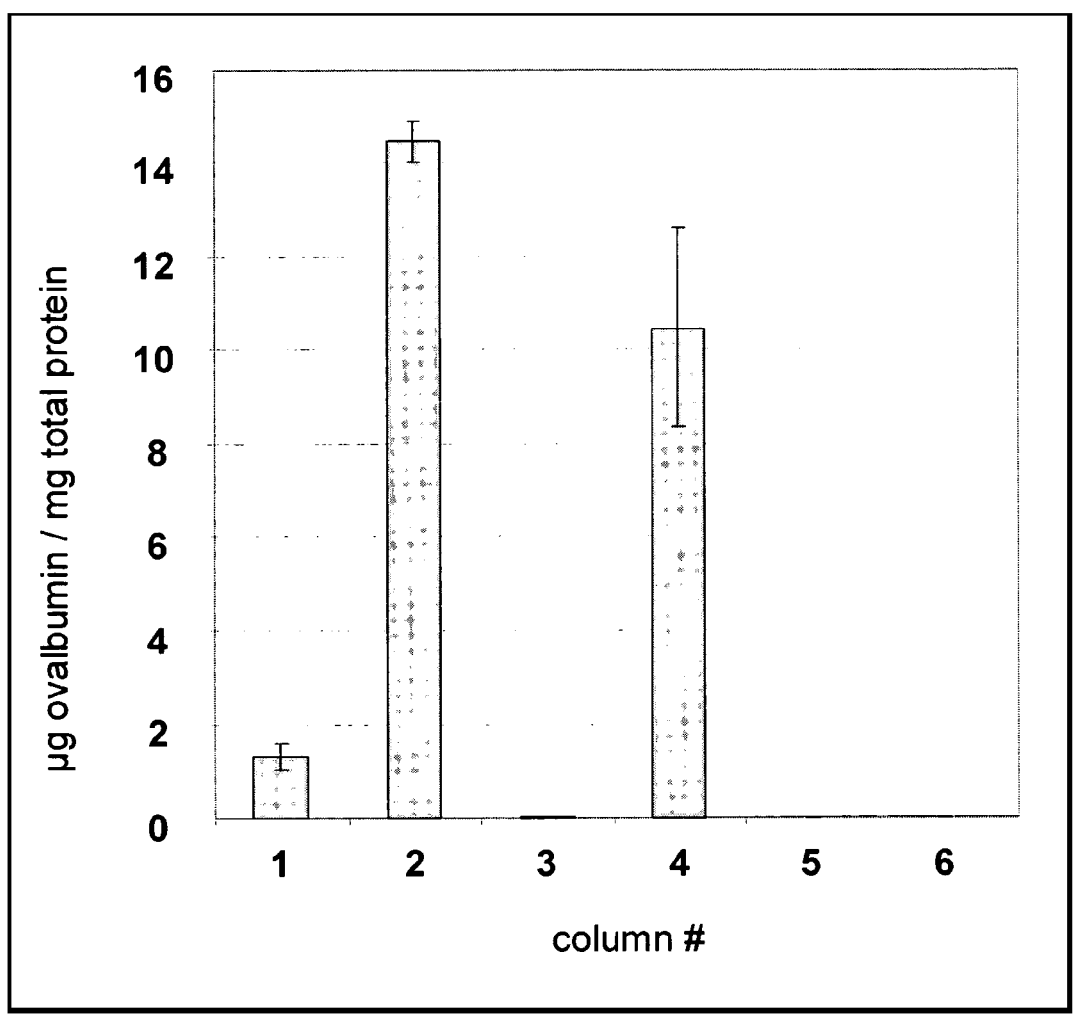
FIG. 1 Expression of the protein ovalbumin ("OVA") in the presence of various combinations of the early/late promoter PrS, PrSSL (SEQ ID NO: 1) and late promoter-inhibiting agent araC (arabinosyl cytosine, an inhibitor of DNA synthesis) as compared to MVA-BN® controls with and without araC. Expression is measured with a commercially available, quantitative, ovalbumin-specific ELISA (SERAMUN DIAGNOSTICA) and total protein is measured with a commercially available BCA assay (UPTIMA). The expression values are calculated as µg ovalbumin expression per mg of total protein. Column 1: PrS-OVA+araC. Column 2: PrS-OVA. Column 3: PrSSL-OVA+araC. Column 4: PrSSL-OVA. Column 5: MVA-BN® (empty vector control)+araC. Column 6: MVA-BN® (empty vector control) without araC. The Y axis depicts µg ovalbumin expression per mg of total cell protein, with higher numbers representing more protein production, i.e. higher expression. Column 4 (PrSSL-OVA) indicates the activity of SEQ ID NO: 1 as a promoter, since expression of the ovalbumin protein in MVA requires a promoter, and no other promoter was present besides PrSSL. Column 3 (PrSSL-OVA+araC) indicates the activity of SEQ ID NO: 1 as a late promoter, since araC is known to inhibit the activity of promoters late but not early in the MVA life cycle.

As stated above, in one aspect the invention provides a promoter selected from the group of nucleic acids consisting of:

(a) a nucleic acid having a nucleotide sequence as set out in SEQ ID NO: 1 ("PrSSL", respectively);
(b) a nucleic acid having a nucleotide sequence derived from the nucleic acid set out in (a), comprising at least one nucleotide addition, deletion, substitution and/or inversion as compared to the nucleotide sequence of (a) and having essentially the same expression characteristics as the nucleic acid of (a);
(c) a nucleic acid sequence having at least 70% identity with the nucleic acid of (a) and having essentially the same expression characteristics as the nucleic acid of (a); and
(d) a nucleic acid capable of hybridizing to a nucleic acid sequence of (a), (b) or (c) and having essentially the same expression characteristics as the nucleic acid of (a).

Preferably, the promoter has a length of up to and including 27 nucleotides.

The invention is based on the surprising finding that the sequence as set out in SEQ ID NO: 1 and related sequences, efficiently function as late promoters of gene expression in pox viral, in particular, vaccinia viral systems, especially MVA. The term "late promoter" refers to any promoters that are active after viral DNA replication has taken place. The promoters of the invention are unique as promoters due to their very short length. For example, SEQ ID NOs: 1 (PrSSL), 33 or 34 comprise only 16 nucleotides, and are thus much shorter in length than other known vaccinia promoters. This extreme shortness implies several distinct advantages over other known vaccinia viral promoters.

First, the stability of a nucleic acid sequence is generally inversely proportional to its length. Thus, a longer nucleic acid sequence would generally be expected to be less stable in vivo, where a shorter nucleic acid sequence would generally be expected to exhibit greater stability in vivo. Given that a promoter is generally a mandatory element of a recombinant expression system in vaccinia, the promoter cannot be omitted without forfeiting the desired expression of the gene construct. By greatly reducing the size of this mandatory promoter element in PrSSL and related promoter sequences, the inventors have thus greatly improved the stability of the resulting genetic construct, thereby ensuring continued high expression levels in vivo which will not attenuate over time.

Second, PrSSL and related sequences having essentially the same expression characteristics as SEQ ID NO: 1, respectively, are more easy to synthesize as part of an extended expression cassette in vaccinia than other known promoters.

Moreover, it is generally known that the frequency of homologous recombination between two genes is proportional to the distance between two linked genes. Further, since each nucleotide within a given sequence is associated with a certain statistical probability of recombination, longer homologous sequences, by virtue of containing more nucleotides, will generally be more prone to recombination which can potentially lead to instable or non functional viruses. Conversely, shorter sequences imply a lower probability of recombination, which makes them more stable. The extremely short length of the promoter given by PrSSL and related promoters having essentially the same expression characteristics renders these promoters much less prone to recombination within the vaccinia genome—and thus more likely to lead to continued high protein expression levels—than other known, longer promoters. When the vaccinia virus is to be used as a vaccine, this increased amount of expression manifests itself in an increased immunogenicity of the antigenic protein produced, since a higher effective protein titer is generated.

Finally, the promoter activity of PrSSL and related promoters having essentially the same expression characteristics is very strong. For example, it has been observed (see Examples and corresponding figures) that the promoter activity of PrSSL is approximately ⅔ that of PrS. PrS is one of the strongest known promoters, if not the strongest.

As used herein, the term "promoter" denotes a regulatory region of nucleic acid, usually DNA, located upstream of the sequence of a nucleic acid to be expressed, which contains specific DNA sequence elements, that are recognized and bound e.g. by protein transcription factors and polymerases responsible for synthesizing the RNA from the coding region of the gene being promoted. Thus, the promoter sequence may comprise nucleotides until position −1. However, nucleotides from position +1 are not part of the promoter, i.e. in this regard it has to be noted that the translation initiation codon (ATG or AUG) is not part of the promoter. Thus, SEQ ID NO:2 and 3 are polynucleotides comprising the promoter of the invention and additionally, the translation initiation codon ATG with optional further nucleotides. This numbering of the nucleotides has been depicted in Table 1. It has to be further noted, that the positions given here for the promoter and polynucleotides do not necessarily reflect positions, which are in connection with mRNA positions.

As used herein, a nucleotide sequence having "essentially the same expression characteristics" as the nucleotide sequence set out in SEQ ID NO: 1 will exhibit at least 70%, preferably at least 80%, even more preferably at least 90% of the promoter activity of SEQ ID NO: 1, as measured by amount of recombinant protein produced. Whether or not a promoter sequence in question has "essentially the same expression characteristics" as any of SEQ ID NO: 1 may be readily determined by one of ordinary skill in the art using the method set out in Example 1 of the present application. The promoters according to the present invention are preferably active as pox virus promoters, preferably vaccinia virus promoters or active as promoters in pox virus infected cells, preferably vaccinia virus infected cells. The vaccinia virus is preferably MVA, in particular one of the MVA strains as specified below. "Active as pox virus promoter" means that the promoter is able to direct the expression of a gene to which it is operably linked in a pox virus after infection of cells with said virus. The cells are preferably cells that allow late and/or early and/or early/late expression of the pox virus. "A promoter active in pox virus infected cells" includes also the situation in which the promoter is not part of a pox virus genome, e.g. part of a plasmid or linear polynucleotide or a non-pox virus viral genome; in such a situation the promoter according to the present invention is active if the cell comprising the promoter also comprises a pox virus genome, e.g. if the cell is infected with a pox virus. Under these circumstances the viral RNA polymerase recognizes the promoter according to the present invention and the expression of the gene/coding sequence that is linked to the promoter is activated.

As used herein, the term "derived from the nucleic acid set out in SEQ ID NO: 1" means that the nucleotide sequence of SEQ ID NO: 1 is taken as a basis for effecting the nucleotide modifications specified, for example, at least one nucleotide addition, deletion, substitution and/or inversion. The term "derived" includes the possibility, for example, of actually modifying the physical sequence corresponding to SEQ ID NO: 1 by known methods, for example, error-prone PCR. The term "derived" additionally includes the possibility of performing modifications on the sequence of SEQ ID NO: 1 in silico, and then synthesizing the thus determined sequence as a physical nucleic acid. For example, the term "derived" encompasses the possibility of using any known computer program for the analysis of nucleic acid sequences with regard to, for example, hybridization stability and the possibility of any secondary nucleic acid structure in modifying the starting sequence of SEQ ID NO: 1. Preferably, not more than 10, 9, 8, 7, 6, 5, 4, 3, 2 or 1 nucleotides have been added, deleted, substituted and/or inverted from the nucleic acids of SEQ ID NO: 1. Furthermore, addition, insertion or deletion of at least one nucleotide should not result to a start codon of the nucleic acid to be expressed. Examples of such promoters which have been derived from the nucleic acid set out in SEQ ID NO: 1 are e.g. SEQ ID NO: 33 (aatttttaatctataa) or SEQ ID NO:34 (atttttatt ctataa).

As used herein, the terms "expressed", "express", "expression" and the like denote the transcription alone as well as both the transcription and translation of a sequence of interest. Thus, in referring to expression of a nucleic acid present in the form of DNA, the product resulting from this expression may be either RNA (resulting from transcription alone of the sequence to be expressed) or a polypeptide sequence (resulting from both transcription and translation of the sequence to be expressed). The term "expression" thus also includes the possibility that both RNA and polypeptide product result from said expression and remain together in the same shared milieu. For example, this is the case when the mRNA persists following its translation into polypeptide product.

One aspect of the invention includes promoters with nucleic acids having at least 70%, preferably 75%, 80%, 85%, 90% or 95% identity with SEQ ID NO: 1 and having essentially the same expression characteristics as SEQ ID NO: 1. For example, the recognition of the promoter activity of SEQ ID NO: 1 ("PrSSL"), which is not part of any known pox viral genome, allowed the further recognition of similar corresponding promoters in MVA (128L gene) and other poxviruses such as vaccinia virus (A18L gene), chorioallantois virus Ankara CVA (CVA144 gene), shope fibroma virus SFV (s107L gene) and the human pathogenic variola virus (A18L gene). In each case, a sequence similar but not identical to PrSSL is located upstream of the open reading frame, wherein positions −15 and −16 (see Table 1) are the most variable positions relative to SEQ ID NO: 1.

A BLAST search of the NCBI database using a polynucleotide comprising SEQ ID NO: 1 and further nucleotides comprising the start codon as a query sequence, followed by analysis of the first 1000 database hits, indicated a number of sequences in which nucleotide position −15 was altered relative to SEQ ID NO: 1. The virus strains in which such alterations were found include different strains of vaccinia virus, chorioallantois virus Ankara, modified vaccinia virus Ankara, myxoma virus, tanapox virus, ectromelia virus, camelpox virus, horsepox virus, cowpox virus, taterapox virus, goatpox virus, sheeppox virus, deerpox virus, monkeypox virus, yaba monkey tumor virus, lumpy skin disease virus, swinepox virus, variola major virus, variola minor virus, and yaba-like disease virus. In addition to variability at positions −15 and −16, position +4 was also found exhibit variability relative to a polynucleotide comprising SEQ ID NO: 1 and further nucleotides including the start codon. Numbering of the positions is as indicated in Table 1.

A further aspect of the invention relates to a nucleic acid capable of hybridizing to a nucleic acid sequence of (a), (b) or (c) and having essentially the same expression characteristics as the nucleic acid of (a). The term "capable of hybridizing" means hybridization in conditions in which any portion of the nucleic acid of (a), (b) or (c) is able to hybridize to another DNA sequence to allow detection and isolation of any DNA sequence having essentially the same expression characteristics as the nucleic acid of (a). The hybridization is carried out in stringent conditions; the more stringent the conditions, the more likely partially complementary sequences are to be forced apart, i.e. higher stringency lowers the probability of hybridization. In practise, the term "stringent conditions" means hybridization conditions with high temperature (e.g. 65° C.) and/or low salt concentration (e.g. 0.1×SSC). Increasing the temperature and/or decreasing the salt concentration increases the stringency. Under stringent conditions hybridization will occur only if there is at least 70% or preferably at least 75, 80, 85, 90 or 95% identity between the sequences. Hybridization can be carried out as set out in Ausubel et al. (2002) Short Protocols in Molecular Biology Vol. 1 5$^{th}$ ed. Canada.

Preferably, the promoter of the invention has a length of up to and including 27 nucleotides, i.e. below 28 nucleotides. Even more preferably, the promoter of the invention has a length of up to and including 26 nucleotides, i.e. below 27 nucleotides or a length of up to and including 25 nucleotides, i.e. below 26 nucleotides. In one embodiment, the nucleic acid of (b), (c) or (d), as set out above, comprises about 5-25 nucleotides, about 6-24 nucleotides, about 7-23 nucleotides, about 8-22 nucleotides, about 9-21 nucleotides, about 10-20 nucleotides, about 11-19 nucleotides, about 12-18 nucleotides or about 13, 14, 15, 16 or 17 nucleotides. Further, preferred embodiments are promoters having a length of 10-27 nucleotides, 10-26 nucleotides, 10-25 nucleotides, 14-23 or 15-20 nucleotides. Even the longest of these possible promoter lengths lies well below the generally known and accepted length of a promoter in the prior art. For example, the shortest poxviral promoter known to the inventors, I1R, is 27 nucleotides long but does not exhibit the same high promoter activity as compared to PrS. However, even this short length is an exception, and most known promoters are longer, on the order of 30-100 nucleotides. In an especially preferred embodiment, the promoter consists of 16-25 nucleotides.

In one embodiment, the invention is related to a polynucleotide comprising a promoter as set out above. In a preferred aspect of this embodiment at least one further nucleotide is added from position +1, i.e. added downstream from the promoter. In one embodiment of this aspect, the polynucleotide of the invention comprises the promoter as set out above with start codon ATG or AUG (positions +1 to +3) of the nucleic acid to be expressed. Examples of such polynucleotides with start codon are SEQ ID NOs. 2 and 3. Here, it is preferred that position +4 of the nucleic acid to be expressed is G or A. Example of such a polynucleotide is SEQ ID NO:2. In a further preferred embodiment, the polynucleotide comprises a TAAAT motif at positions −3 to +2, examples of such polynucleotides are SEQ ID NOs:2, 3, 4 and 5.

In a further embodiment, the promoter of (b), as set out above, contains an AT-content or AU-content of at least 70%, at least 75%, at least 80%, at least 85%, at least 90%, at least 95% or 100%. The sequence of PrSSL was determined by analyzing 24 different MVA genes assumed to yield high expression levels of recombinant protein.

As used herein, the term "AT-content" or "AU-content" refers to the cumulative content of all adenine and thymine, or adenine and uracil nucleotides in a given sequence, based on the total length of the respective sequence (e.g. PrSSL or related promoters having essentially the same expression characteristics) including the nucleotides A, T and U. For example, the percent AT content or AU content of a sequence in question may be calculated by dividing the combined number of the nucleotides A and T (for DNA) or A and U (for RNA) in a sequence in question by the total number of nucleotides in the sequence in question (including those already counted above), and multiplying the result by 100.

In a further aspect, the invention provides a polynucleotide comprising a nucleic acid to be expressed and a promoter as set out above. For example, the promoter included in the polynucleotide according to the invention may be a nucleic acid having a nucleotide sequence as set out in any of SEQ ID NOs: 1, 33 or 34 or may be a nucleic acid sequence having at least 70% identity with SEQ ID NO: 1 and essentially the same expression characteristics as SEQ ID NO: 1, as determined by the method set out in Example 1. The promoter comprised in the polynucleotide may also for example be a nucleic acid having a nucleotide sequence derived from SEQ ID NO: 1, comprising at least one nucleotide addition, deletion, substitution and/or inversion as compared to the sequence of SEQ ID NO: 1 and having essentially the same expression characteristics as SEQ ID NO: 1, as determined by the method set out in Example 1. In one aspect of this embodiment, the polynucleotide construct may comprise a polynucleotide comprising the promoter of the invention with further nucleotides added from position +1, preferably any of the SEQ ID NO 2-5, and a nucleic acid to be expressed.

In one embodiment, the polynucleotide comprising both the nucleic acid to be expressed and the promoter as set out above comprises the promoter in a form joined directly to the start codon ATG or AUG of the nucleic acid to be expressed. As with other vaccinia/MVA sequences, the polynucleotide will generally exist in the form of DNA, meaning that the start codon will be ATG. In some rarer cases, however, it is observed that part of the promoter lying directly upstream of the start codon is transcribed into RNA, and that this transcription continues into the nucleic acid region encoding the protein to be expressed. In such as case, at least part of the promoter as set out above, when directly joined to the start codon, may be present in the form of RNA, in which case this RNA would be joined to an "AUG" start codon. It has to be noted that by definition the start codon ATG or AUG is not part of the promoter sequence.

As used herein, the term "upstream" refers to the 5' direction on a nucleic acid, and the term "downstream" refers to the 3' direction on a nucleic acid. For example, if sequence X is located "upstream" of sequence Y in the same nucleic acid, this means that sequence X is located 5' of sequence Y, or conversely, that sequence Y is located 3' of sequence X.

In another embodiment, the promoter comprised in the polynucleotide is separated from the start codon ATG or AUG by a non-transcribed region of about 1, 2, 3, 4, 5, 6, 7, 8, 9, 10, from about 10-20, from about 20-30, from about 30-40, from about 40-50, from about 50-100 or from about 100-200 nucleotides, which does not include the start codon ATG or AUG. It is well known, and has been observed for promoters of the present PrSSL series and related sequences that the sequence responsible for transcription need not be located directly adjacent to the start codon (although this is possible), but may also be located rather far upstream from the actual sequence to be expressed.

In this embodiment, where the promoter is joined to the nucleic acid to be expressed via an intervening nucleic acid of some length, it is advantageous that the polynucleotide comprising the promoter has the sequence TAAAT at positions −3 to +2 (as for example in SEQ ID NO: 4), or even more preferred that the polynucleotide comprising the promoter has the sequence TAAATA at positions −3 to +3 (as for example in SEQ ID NO: 5).

Even though in this embodiment the promoter of the invention is separated from the start codon ATG or AUG, preferably the ATG start codon of the polynucleotide to be expressed is directly followed by a G, thus, allowing a high expression.

As used herein, the term "about" denotes an approximation of a given value and may be interpreted as denoting a variance on the order of 10% greater or less than the specified value. Where appropriate, for example in calculating nucleotide length where fractional nucleotides are impossible, the skilled person understands that the term "about" entails rounding up or down to the nearest whole nucleotide. For example, "about 16 nucleotides" implies a variance of, say, 10% greater and less than this value, leading mathematically to a length of 14.4 nucleotides or 17.6 nucleotides, each of which is impossible. The skilled person thus understands that, in this example, 14.4 nucleotides would be rounded down to 14 nucleotides and 17.6 nucleotides would be rounded up to 18 nucleotides.

In one embodiment, the nucleic acid to be expressed comprises an open reading frame ("ORF") encoding a polypeptide to be translated.

As used herein, the term "open reading frame" or "ORF" denotes a nucleotide sequence encoding a polypeptide, where the "A" of the start codon ATG or AUG in the ORF defines the beginning of the reading frame to be used for translation. The protein to be expressed, i.e. either transcribed and/or transcribed and translated according to the present invention will generally be a recombinant protein. Accordingly, its sequence will generally be dictated by former knowledge of the encoded amino acid sequence. As such, the polynucleotide in the form of DNA will generally include the cDNA encoding the (recombinant) protein of interest in the ORF. The term "ORF" also includes a "partial ORF", that is a nucleotide sequence encoding only a part of a known polypeptide. This may for example be indicated when the epitope to be presented to the host immune system in a vaccine is present only in one part of a known polypeptide. In this case, it may be sufficient to include only the corresponding portion of the known polypeptide as a partial ORF in the polynucleotide.

In a further embodiment, where the promoter is joined directly to the ATG or AUG start codon of the nucleic acid to be expressed, this ATG or AUG start codon is, by definition (see Table 1), located at positions +1 to +3 of the nucleic acid to be expressed. Here, it is preferred that position +4 of the nucleic acid to be expressed is G or A. This corresponds to the first nucleotide in the nucleotide triplet encoding the second amino acid in the polypeptide to be expressed. Accordingly, incorporation of "G" at position +4 may not always be possible if this incorporation, when translated, would lead to a different amino acid than desired or necessary at position 2 of the polypeptide to be expressed. However, the skilled person understands that the degeneracy of the genetic code often allows substitution of one nucleotide for another within a given triplet codon, without changing the identity of the translated amino acid. The skilled person also understands that even when a nucleotide substitution does change the identity of a resulting amino acid at a given position, this need not affect the overall folding and thus epitope distribution on a given polypeptide. Therefore, whether the above advantages obtained in substituting a "G" or an "A" at position +4 of the coding strand offset any disadvantage incurred in possibly altering the identity of the amino acid at position 2 of the expressed polypeptide is a question which must be assessed on a case-by-case basis given the known sequence of the polypeptide and the importance of amino acid 2 in eliciting the desired immune response. SEQ ID NO: 2 is an example of an inventive polynucleotide which is located directly adjacent to the ATG start codon of the nucleic acid to be expressed, and in which position +4 is G.

In a further embodiment, the polynucleotide comprises at least two promoters, at least one of which is a promoter as set out in SEQ ID NO: 1 or a related promoter with essentially the same expression characteristics as described herein. For example, PrSSL may be joined in homo-tandem with one or more units of PrSSL, or in hetero-tandem with one or more units of any of related promoters having essentially the same expression characteristics. The same applies for possible homo- and hetero-tandems of any of PrSSL or related promoters having essentially the same expression characteristics. Preferably the at least two promoters are operably linked with one another.

In a further preferred embodiment the polynucleotide comprises at least two promoters, at least one of which is promoter as set out in SEQ ID NO: 1 or a related promoter with essentially the same expression characteristics as described herein and at least one of the promoters is an early promoter. The term "early promoter" refers to promoters that are active in pox virus or poxvirus infected cells, before viral DNA replication has occurred. Preferred examples of early promoters of vaccinia virus are the 7.5 kDa early promoter (fragment of the Pr7.5K promoter) and the TK promoter (Thymidine Kinase).

The invention further provides a vector comprising a promoter as set out above and/or a polynucleotide as set out above.

In one embodiment, the vector is a polynucleotide vector. The term "polynucleotide vector" refers to any vectors known to the person skilled in the art. The polynucleotide vector may for example be linear DNA, circular DNA (e.g. plasmid DNA such as for example pBR322 or any vector of the pUC series), or artificial DNA.

For example, a plasmid vector according to the present invention may comprise a DNA sequence derived from or homologous to the genome of, for example, a viral vector, in particular, MVA or MVA-BN®, wherein said DNA sequence comprises a complete or partial fragment of a sequence to be expressed located between or flanked by two adjacent sequences of the viral genome. Preferably, the viral genome comprises at least one cloning site for the insertion of the sequence to be expressed and, preferably, for the insertion of a pox viral transcription control element such as any of the promoters described hereinabove, operatively linked to the nucleic acid to be expressed.

In another embodiment, the vector is a virus vector. As used herein, the terms "viral vector" or "virus vector" refer to an infectious and/or attenuated virus comprising a viral genome. In this case, the nucleic acid of the present invention is part of the viral genome of the representative viral vector and/or constitutes the viral genome. The recombinant vectors can be used for the infection of cells and cell lines, in particular, for the infection of living animals including humans. Typical virus vectors according to the present invention are adenoviral vectors, retroviral vectors or vectors on the basis of the adeno-associated virus 2 (AAV2). Most preferred are pox viral vectors. The pox virus may be preferably a canary pox virus, a fowl pox virus or a vaccinia virus.

In a preferred embodiment, the viral vector is modified vaccinia virus Ankara (MVA) (Sutter et al. (1994), Vaccine 12, 1032-1040). A typical MVA strain is MVA 575 that has been deposited with the European Collection of Animal Cell Cultures under the deposition number ECACCV00120707. Most preferred is an MVA strain that has the capability of reproductive replication in vitro in chicken embryo fibroblasts (CEF), but no capability of reproductive replication in the human keratinocyte cell line HaCaT, the human embryo kidney cell line 293, the human bone osteosarcoma cell line 143B, and the human cervix adenocarcinoma cell line HeLa. In a further preferred embodiment, the MVA strain fails to replicate in a mouse model that is incapable of producing mature B and T cells and as such is severely immune compromised and highly susceptible to a replicating virus. Further preferred is an MVA strain which induces at least the same level of specific immune response in vaccinia virus prime/vaccinia virus boost regimes when compared to DNA-prime/vaccinia virus boost regimes. Most preferred is an MVA strain comprising all three of the above-mentioned properties. All such most preferred MVA strains, in the following generally referred to as "MVA-BN®", have been described in the PCT application PCT/EP01/13628 filed at the European Patent Office on Nov. 22, 2001, entitled "Modified Vaccinia Ankara Virus Variant". A sample of MVA-BN® has been deposited at the European Collection of Animal Cell Cultures with the deposition number ECACC V00083008. By using MVA-BN®, the protein to be expressed may be expressed in an extremely attenuated and therefore safe virus, which is derived from modified vaccinia Ankara virus and which is characterized by the loss of its capability to reproductively replicate in human cells. MVA-BN® is safer than other known vaccinia virus strains due to a lack of replication in humans. In a further most preferred embodiment, the viral vector containing the promoter as set out above, or the polynucleotide as set out above is MVA-BN® as deposited at the European Collection of Animal Cell Cultures with the deposition number ECACC V00083008. The features of MVA-BN®, the description of biological assays allowing one to evaluate whether an MVA is MVA-BN® and methods allowing one to obtain MVA-BN® are disclosed in the above-referenced PCT application PCT/EP01/13628, which is herewith incorporated by reference.

In another aspect the invention further provides a host cell comprising a promoter as set out above, a polynucleotide as set out above and/or a vector as set out above. Preferably, the host cell is a cell in which the virus is able to replicate such as CEF cells or a cell that can be infected by MVA, but in which the virus does not replicate (such as the types of human cell lines which are mentioned above for MVA-BN®).

In a further aspect of the invention, promoters, polynucleotides, vectors and host cells as described above may also be made part of a composition, preferably a pharmaceutical composition. For increased readability, the composition in the following is assumed to comprise MVA or MVA-BN® comprising a promoter of SEQ ID NO: 1 or a related promoter having essentially the same expression characteristics, but the skilled person will appreciate that the composition may alternatively or additionally comprise any of the promoters described hereinabove, any of the polynucleotides described hereinabove or any of the vectors which are not MVA or MVA-BN® described hereinabove.

In one embodiment, the composition is a vaccine composition. This vaccine composition may be advantageously used to introduce one or more homologous or one or more heterologous sequence(s) into cells and may be applied as part of in vitro or in vivo therapy. For example, the composition may comprise isolated cells which have been previously (ex vivo) infected with e.g. the recombinant MVA comprising the promoter of SEQ ID NO:1 according to the invention or related promoters having essentially the same expression characteristics. Such a cell-containing composition is preferably suitable for administration to the living animal body for affecting, preferably inducing an immune response.

Alternatively or additionally, the composition may comprise a recombinant pox virus such as a recombinant MVA or MVA-BN® comprising a promoter, polynucleotide or vector as described hereinabove, and is preferably suitable for administration to the living animal body for affecting, preferably inducing an immune response. In this case, the cells surrounding the site of inoculation, but also cells where the virus is transported to via for example the bloodstream are directly infected in vivo by the recombinant MVA according to the invention. After infection, these cells synthesize the proteins, peptides or antigenic epitopes (for example partial peptides) of the therapeutic genes, which are encoded by the exogenous coding sequences and, subsequently, present them or parts thereof on the cellular surface. Specialized cells of the immune system recognize the presentation of such heterologous proteins, peptides, epitopes and launch a specific immune response.

The present invention thus also provides pharmaceutical compositions and vaccines suitable for inducing an immune response in a living animal body, including a human. The pharmaceutical composition may generally include one or more pharmaceutically acceptable and/or approved carriers, additives, antibiotics, preservatives, adjuvants, diluents and/or stabilizers. Such auxiliary substances can be water, saline, glycerol, ethanol, wetting or emulsifying agents, pH buffering substances, or the like. Suitable carriers are typically large, slowly metabolized molecules such as proteins, polysaccharides, polylactic acids, polyglycolic acids, polymeric amino acids, amino acid copolymers, lipid aggregates, or the like.

For the preparation of vaccines, the (pharmaceutical) composition is converted in one embodiment into a physiologically acceptable form. For example, in the event that the (pharmaceutical) composition comprises a pox virus, preferably MVA with the inventive promoter of SEQ ID NO: 1 or a related promoter with essentially the same expression characteristics, conversion into physiologically active form can be performed based on the experience in the preparation of pox virus vaccines used for vaccination against smallpox (as described by Stickl et al. (1974) Deutsche medizinische Wochenschrift 99, 2386-2392). For example, the purified virus is stored at −80° C. with a titre of $5\times10^8$ TCID$_{50}$/ml (tissue culture infectious dose per milliliter) formulated in about 10 mM Tris, 140 mM NaCl, pH 7.4-pH 7.8, e.g. pH 7.4 or pH 7.7. For the preparation of vaccine shots, for example, $10^2$-$10^8$ particles of the virus are included in 100 ml of phosphate buffered saline ("PBS") in the presence of 2% peptone and 1% human albumin in an ampoule, preferably a glass ampoule. Alternatively, the vaccine shots can be produced by stepwise freeze-drying of the virus in a formulation. This formulation can contain additional additives such as menathol, dextrin, sugar, glycine, lactose or polyvinylpyrrolidone or other aids such as antioxidants or inert gas, stabilizers or recombinant proteins (for example, human serum albumen) suitable for in vivo administration. The glass ampoule is then sealed and can be stored between 4° C. and room temperature for several months. However, as long as no need exists, the ampoule is preferably stored at temperatures below −20° C.

For vaccine or therapy, the MVA comprising the promoter of SEQ ID NO: 1 or related promoters as described hereinabove can be dissolved in 0.1 to 0.5 ml of an aqueous solution, preferably physiological saline or Tris buffer, and administered either systemically or locally, i.e. parenterally, subcutaneously, intramuscularly, by scarification or any other path of administration known to the skilled practitioner. The mode of administration, the dose and the number of administrations can be optimized by those skilled in the art in an known manner. However, most commonly the subject is vaccinated with a second shot about one month to six weeks after the first vaccination shot.

If the vaccine is a vaccinia virus, in particular, MVA, in particular, MVA-BN®, a typical vaccine shot for humans comprises at least $10^2$, preferably at least $10^4$, preferably at least $10^6$, even more preferably $10^7$ or $10^8$ TCID$_{50}$ of the virus.

If the vaccine is a recombinant MVA, in particular, recombinant MVA-BN®, the virus may be used for prime-boost administration. Thus, the invention further relates to a method, wherein the vector is MVA, in particular, MVA-BN® comprising the promoter of SEQ ID NO:1 or a related promoter as described hereinabove, and wherein said vector or the composition or the vaccine comprising said vector is administered to an animal, including a human in need thereof, in therapeutically effective amounts in a first inoculation ("priming inoculation"), in a second inoculation ("boosting inoculation") and/or an additional third or further inoculation.

A further aspect of the invention provides the use of a promoter as set out above, a polynucleotide as set out above, a vector as set out above, a host cell as set out above and/or a composition as set out above for expressing a nucleic acid, preferably a gene.

A still further aspect of the invention provides the use of a promoter as set out above, a polynucleotide as set out above, a vector as set out above, a host cell as set out above and/or a composition as set out above in the preparation of the medicament for inducing an immune response or for the treatment or the prophylaxis of cancer and/or an infectious disease.

In addition, the invention provides the promoter of the invention, a polynucleotide as set out above, a vector as set out above, a host cell as set out above and/or a composition as set out above for inducing an immune response or for the treatment or the prophylaxis of cancer and/or an infectious disease.

Ideally, the cancer treated or prevented by the medicament is chosen from the group consisting of: AIDS-related cancers (e.g. AIDS-related lymphoma), breast cancer, colon cancer, kidney cancer, leukemia, liver cancer, lung cancer, lymphoma, skin cancer (e.g. melanoma), ovarian cancer, pancreatic cancer, prostate cancer, retinoblastoma, squamous cell carcinoma, squamous neck cancer, stomach (gastric) cancer, testicular cancer and thyroid cancer.

Ideally, the infectious disease treated or prevented by the medicament is chosen from the list consisting of: viral infectious diseases, bacterial infectious diseases, parasitic infectious diseases, fungal infectious diseases and prion infectious diseases.

In an especially preferred embodiment, the medicament is a vaccine. Properties of recombinant vaccines as well as formulations and suitable dosing regimens thereof are set out hereinabove.

In a further aspect, the invention further provides a method for preparing a polypeptide comprising (a) providing a polynucleotide as set out above, where the nucleic acid to be expressed contains an ORF or a partial ORF; (b) subjecting the polynucleotide of (a) to conditions conducive to transcription and translation of the nucleic acid to be expressed; (c) recovering a polypeptide; and (d) optionally purifying the polypeptide.

As used herein, the term "conditions conducive to transcription and translation" may for example include introduction of a polynucleotide as described above, e.g. by means of a recombinant virus, preferably MVA, with a multiplicity of infection of preferably 10, into e.g. HeLa cells, followed e.g. by incubation at 37° C. under 5% $CO_2$ for 24 to 48 h in growth medium, e.g. Dulbecco's Modified Eagle Medium (DMEM) with 10% fetal calf serum (FCS). These and other suitable conditions are well known to the skilled practitioner.

In accordance with this aspect, the advantageous properties of the inventive promoter may be exploited in the production of virtually any desired polypeptide. Ideally, the polypeptide will be prepared in a viral vector-dependent expression system. For example, this may be an expression system exploiting the protein expression capability of cells which are infected by a viral vector containing a promoter of SEQ ID NO: 1 or a related promoter having essentially the same expression characteristics, as described hereinabove. The viral vector is advantageously any of the viral vectors set out above, especially MVA or MVA-BN®. Suitable methods for producing and isolating a protein from such cells are known in the art.

In a further aspect, the invention provides a method of expressing a nucleic acid, said method comprising providing a polynucleotide comprising the nucleic acid to be expressed; providing a promoter as set out above operably linked to the nucleic acid to be expressed; and subjecting the thus provided polynucleotide to conditions conducive to the expression of the nucleic acid. As set out above, the term "expressing" or grammatically related terms such as "express" and "expression" may refer to transcription (i.e. production of RNA) or translation (i.e. transcription and synthesis of the encoded polypeptide). The method of this aspect can be carried out in vivo or in vitro. It is to be noted that when expressing the nucleic acid, the promoter can be included in a viral vector, preferably pox viral, in particular vaccinia virus vector. However, if the construct comprising the promoter is in a vector other than pox virus vector (e.g. plasmid) or introduced into a genome, then a pox virus is needed in the host cell as a source of transcription machinery.

A further embodiment of the invention relates to a method for inducing an immune response or for treatment or the prophylaxis of cancer and/or an infectious disease comprising providing an immunogenic composition or vaccine comprising the promoter as set out above, a polynucleotide as set out above, a vector comprising the promoter; and administering the composition or vaccine to a subject animal, including a human. Preferably, the composition including the viral vector as described above is administered in a dose of at least $10^2$ $TCID_{50}$, more preferably, $10^7$-$10^8$ $TCID_{50}$ (tissue culture infectious dose). Preferably, the composition of this embodiment can be administered in a first inoculation ("priming inoculation") and in a second inoculation ("boosting inoculation"). In some aspects, also an additional third or further inoculation may be preferred.

The present invention will now be illustrated by the following non-limiting examples.

Example 1

Promoter Activity of SEQ ID NO: 1

To test for promoter activity, a strain of MVA-BN® was engineered containing the promoter of SEQ ID NO: 1 operatively linked with an open reading frame encoding for the ovalbumin ("OVA") protein. The level of ovalbumin production resulting from expression using the promoter of SEQ ID NO: 1 (PrSSL) was to be taken as an indicator (a) of the ability of PrSSL to promote expression of a desired gene, and (b) the magnitude of such expression promotion. The PrS-OVA construct was used as a positive control and to estimate the relative strength of expression of PrSSL.

The MVA construct was prepared as follows: The recombinant MVA-BN® viruses of this study were designed to have the OVA reporter gene in the same integration site (intergenic region between genes 07 and 08 of MVA-BN, as described in WO 03/097845) and in the same orientation. Moreover, downstream of the OVA cassette, a selection cassette with a chemical selection marker and a fluorescence marker is included. This part is identical in all of the recombinant MVA-BN® viruses tested. The constructs differ only in the region upstream of the open reading frame (ORF).

The sequence of PrSSL was fused upstream of the OVA ORF by PCR using a primer which includes (from 5' to 3') a BspEI restriction site directly followed by the PrSSL sequence and then the start codon and the stretch of sequence of the OVA gene. This results in a direct fusion of PrSSL to the OVA ORF. The downstream primer consisted of a stretch of the 3' end of the OVA gene followed by the stop codon and a Bgl II restriction site (the primer sequence was from the non-coding strand). The primers were used in a PCR and the OVA gene served as the template. The resulting PCR product was cloned into the Bsp EI and Bgl II of a recombination plasmid. This recombination plasmid includes a selection cassette. The OVA gene and selection cassette together are flanked by stretches of consecutive MVA-BN® sequences, allowing for integration of the OVA gene and selection cassette into the genome of MVA-BN® via homologous recombination. The resulting virus was named PrSSL-OVA.

A further MVA was generated with the well known PrS promoter optimally fused to the start of the OVA ORF. This was done by PCR and the resulting virus was named PrS-OVA PrS-OVA: MluI-PrS-ATG start of OVA
PrSSL-OVA: MluI-BspEI-PrSSL-ATG start of OVA The testing of protein expression was carried out as follows:

Cell seeding: HeLa cells were seeded with $1.5 \times 10^6$ cells per well in a volume of 2 ml of medium in 6-well plates (FALCON). The medium used was DMEM with Glutamax and high glucose (INVITROGEN) supplemented with 10% fetal calf serum (PAA) and 1% gentamicin (INVITROGEN). The cells were seeded 24 h prior to infection and incubated at 37° C. and 5% $CO_2$. This results in 80 to 90% confluency at the time of infection.

Infection: The cells were infected at a multiplicity of infection (moi) of 10 with the respective recombinant virus. For the infection, the supplemented growth medium was removed from the cells and replaced by 500 µl of non-supplemented DMEM containing the respective virus inoculum. After 1 h of gentle rocking at room temperature, the infection medium was removed from the cells and replaced with 1.5 ml supplemented DMEM medium per well.

Cell screening: 24 h post infection or infection/transfection, the E-well plates were examined under an inverted fluorescence microscope for cytopathic effect and expression of green fluorescence protein which served as a control for infection efficiency. A selection cassette with the gene of the green fluorescence protein was present in each of the recombinant viruses used. Infection levels had to be similar for all examined samples in one experiment, otherwise the material was discarded.

Harvest of cells: For cell harvest the growth medium was removed from the cells and replaced by 250 µl ice cold lysis buffer (=PBS (INVITROGEN)+0.1% Triton X-100 (SIGMA)+1 mM Protease Inhibitor (ROCHE)). After incubation for 5 min at room temperature, the cells were scraped from the bottom of the wells into the lysis buffer and the cell-virus suspensions were transferred to 2 ml reaction tubes. The samples were sonicated in a precooled cup horn ultra sonifier (BRANSON) at maximum intensity for 1 minute at 4° C. and stored on ice. For the determination of total protein the samples were diluted 1:10 in lysis buffer.

Determination of total protein: Total protein was determined using a protein quantification kit (BCA assay kit with Reagent A, Reagent B and BSA standard stock solution (2 mg/ml), catalog number UP40840, positive control 200 µg/ml BSA in TBS, catalog number UP36859A; UPTIMA).

Standardization of the samples to total protein: The protein concentration of all samples was adjusted with lysis buffer to a starting concentration of 0.5 or 1 µg/µl.

ELISA for OVA: The expression of OVA in the samples was quantified with an ovalbumin quantification ELISA kit (SERAMUN, catalog number E-041c). The ELISA was performed according to the kit protocol. Several dilutions were made from the standardized samples (between 1:10 and 1:5000 depending on the sample) with diluent from the ELISA kit (SERAMUN DIAGNOSTICA). The optical density (OD) values were determined in 96-well plates with the ELISA Reader at 450 nm (TECAN Sunrise). OVA concentrations in the samples were determined over their OD values using a standard curve prepared from the ovalbumin standard samples contained in the ELISA kit. OVA concentrations were calculated and are given in µg OVA per mg of total protein in FIG. 1.

The results are shown in column 4 (PrSSL-OVA) and column 6 (MVA-BN®) of FIG. 1. FIG. 1 shows the level of protein production along the Y axis, with higher numbers indicating higher levels of protein produced and thus, strength of a respective sequence as a promoter. It is noteworthy that the OVA gene in the recombinant MVA used to obtain the results in column 4 was regulated exclusively by the promoter of PrSSL. Protein expression by cells infected with empty vector MVA-BN® will not be expected. The measured levels in the ovalbumin ELISA for MVA were calculated as zero expression (columns 5 and 6).

Overall, the results of this experiment demonstrate the activity of PrSSL as a promoter. Since the OVA in column 4 of FIG. 1 was obtained using PrSSL, the level of OVA expression shown in this column is a good indication of the promoter activity attributable to PrSSL alone. While this level of protein expression was slightly less than that observed using the known synthetic early/late promoter PrS alone as a promoter (see column 2), it should not be forgotten that PrS is one of the strongest promoters known, and that PrSSL is much shorter than PrS (44 base pairs, without ATG start codon). Thus, the activity of PrSSL as a promoter is slightly less active than PrS, while being potentially more stable in a construct, easier to synthesize and less prone to deleterious recombination with other sequences in the wild type or recombinant MVA genome.

Example 2

Determination of Late Promoter Activity of PrSSL

Following the above experiment, it was then desired to determine approximately when in the MVA life cycle PrSSL is active. Promoters are typically classified as early, late, intermediate or early/late, depending on the time point within the MVA life cycle when they predominantly drive transcription of genes to which they are operatively linked (early/late promotion refers to promotion both in the early and in the late stages of the viral life cycle).

To this end, the experiment performed above was repeated, this time adding arabinose C (araC). araC is a known inhibitor of DNA replication (a prerequisite for late expression), whereas it has little to no effect on early promoter activity. Thus, a decrease in the level of protein expression observed in Example 1 using araC would indicate that PrSSL is a late promoter, whereas unchanged protein expression with araC as compared to the experiment in Example 1 in which araC was lacking, would indicate that PrSSL is an early promoter.

The MVA construct with the ovalbumin-encoding sequence and PrSSL as a promoter was performed as described above in Example 1. The experiment with araC was performed as follows: Infection was performed in a total volume of 500 µl of non supplemented DMEM (INVITROGEN) per 6-well without any additions. Infections were performed in triplicate for araC treatment and in triplicates for non-treated infected cells. After 1 h of gentle rocking at room temperature, the infective medium supernatant was removed from the cells and replaced with 1.5 ml VP-SFM medium per well. The medium of infected cells was supplemented with araC (Cytosine β-D-arabinofuranoside; SIGMA) at a final concentration of 50 µg/ml as indicated. Cell analysis and harvest was done 24 h post infection as described in Example 1. The results shown in FIG. 1 are calculated from three independent experiments.

The results of this experiment are shown in column 3 of FIG. 1. Here, it is clear that the protein expression previously observed in column 4 (without araC) was completely abolished upon addition of araC, indicating that PrSSL is a late promoter. In contrast, the activity of the PrS promoter observed without addition of araC (column 2) cannot be completely blocked by araC (column 1). The residual protein expression observed using PrS with araC (column 1) reflects the remaining expression from the early part of the early/late promoter PrS. This determination relies on the functional classification of promoter elements known in the art such as for example described in Taddie & Traktman (1991). J. Virol. 65, 869-879. Empty vector control with and without araC treatment (columns 5 and 6) were used as reference for background OVA levels and set as zero (no expression).

Example 3

Combination of the PrSSL Promoter with Either of Promoters Pr7.5 or Pr7.5e

As many promoters are known to work in concert with one another to potentiate protein expression beyond what would be obtainable using only either promoter alone, it was desired to determine whether PrSSL is combinable with other known promoters. Here, PrSSL was combined separately in heterotandem with each of the promoters Pr7.5 and Pr7.5e (Pr7.5e is the early-promoter portion of Pr7.5). PrSSL and each of the promoters Pr7.5 and Pr7.5e were separately combined, with either Pr7.5 or Pr7.5e being located upstream of PrSSL. Control constructs included the filler sequence of SEQ ID NO: 6 in place of PrSSL, with either Pr7.5 or Pr7.5e being located upstream of the filler sequence.

The recombination plasmids used in Example 2 could be used to integrate further sequences upstream of the BspEI site. Upstream of the OVA ORF, a MluI and a BspEI restriction site easily allow the insertion of various sequences. These sequences can be of different origin, e.g. synthetic oligonucleotides forming double strands with the respective overhangs to be fused into the MluI- and BspEI-restricted plasmid. In the case of Pr7.5 and Pr7.5e, this resulted in a tandem of either of these sequences and PrSSL both in the same orientation and only separated by the sequence for the BspEI restriction site. This resulted in the constructs with the well known promoter Pr7.5 (of the gene encoding the 7.5 kD protein) and the early promoting part thereof (Pr7.5e) promoter. The Pr7.5 promoter was amplified by PCR adding the respective restriction sequences to the promoter's ends and the Pr7.5e was made by oligo-annealing. The cowpox PrATI promoter was generated by oligo-annealing and the same strategy was applied as for the Pr7.5e promoter. The following constructs were made:

Pr7.5-PrSSL-OVA: MluI-Pr7.5-BspEI-PrSSL-ATG start of OVA
Pr7.5-filler-OVA: MluI-Pr7.5-BspEI-filler sequence-ATG start of OVA
Pr7.5e-PrSSL-OVA: MluI-Pr7.5e-BspEI-PrSSL-ATG start of OVA
Pr7.5e-filler-OVA: MluI-Pr7.5e-BspEI-filler sequence-ATG start of OVA
PrATI-PrSSL-OVA: MluI-PrATI-BspEI-PrSSL-ATG start of OVA
PrATI-filler-OVA: MluI-PrATI-BspEI-filler sequence-ATG start of OVA MVA-BN® constructs containing the above promoter constructs were made as follows: The control virus containing the sequence Pr7.5-filler-OVA was generated by removal of the PrSSL-OVA fusion from the recombination plasmid used for PrS-PrSSL-OVA via restriction cutting with BspEI-Bgl II fragment. The sequence was replaced by a PCR product with a randomly defined filler sequence directly upstream of the OVA coding ORF also prepared to be cut with BspEI-Bgl II. The resulting virus contains the Pr7.5 promoter and the filler sequence followed by the OVA ORF (PrS-filler-OVA). The constructs Pr7.5-PrSSL-OVA, Pr7.5-filler-OVA, Pr7.5e-PrSSL-OVA, Pr7.5e-filler-OVA, PrATI-PrSSL-OVA and PrATI-filler-OVA were made by replacing the PrS promoters from PrS-PrSSL-OVA or PrS-filler-OVA by restriction enzyme digestion with MluI and BspEI.

The experiments with and without araC were performed as indicated above in examples 1 and 2. The results are shown in FIG. 2.

Figure 2:
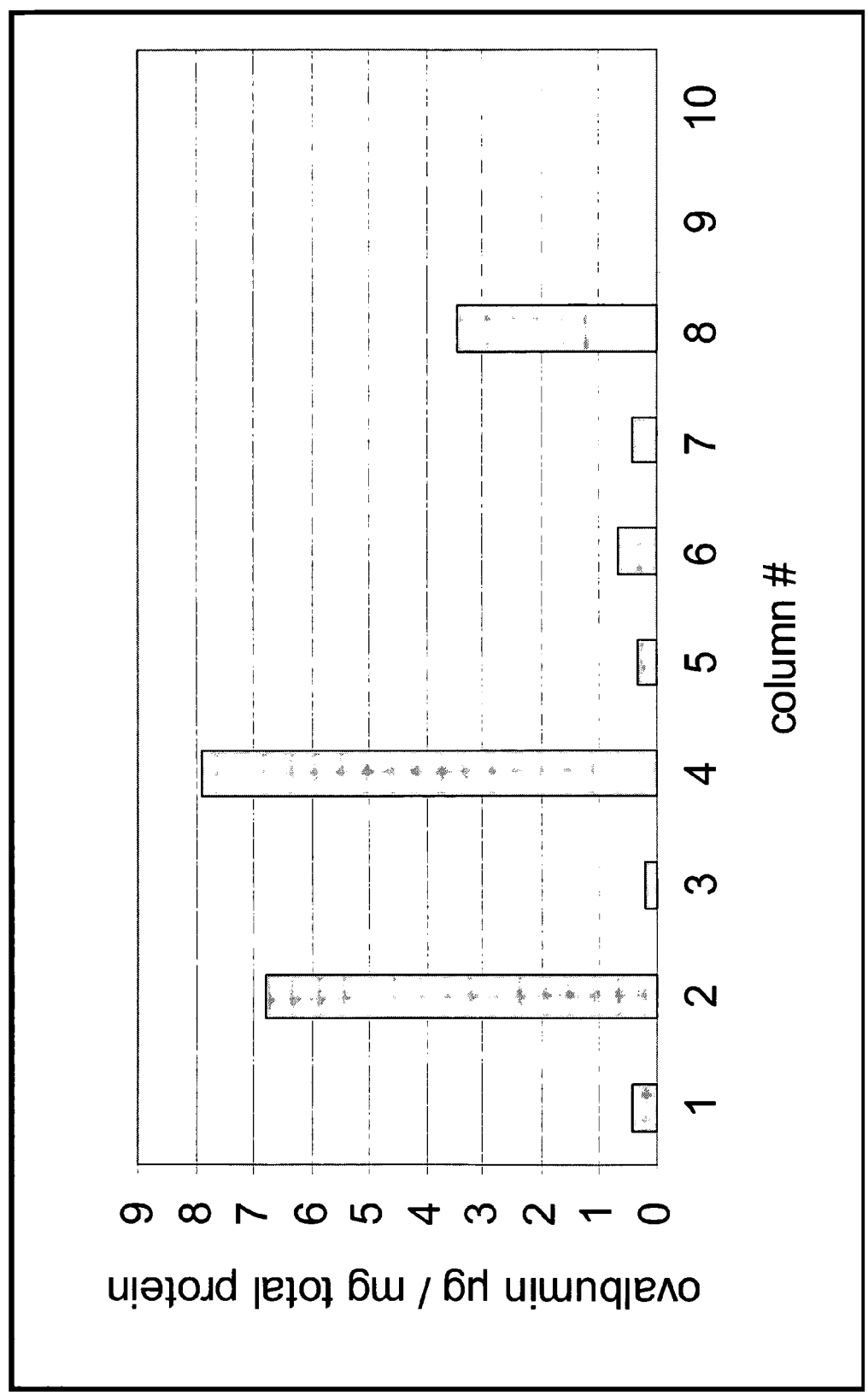
FIG. 2 Expression of the protein ovalbumin ("OVA") in the presence of various combinations of Pr7.5 and Pr7.5e promoters, with either PrSSL or a filler sequence and late-promoter-inhibiting agent araC (arabinosyl cytosine, an inhibitor of DNA synthesis) as compared to MVA-BN® controls with and without araC. Expression is measured with a commercially available quantitative ovalbumin specific ELISA (SERAMUN DIAGNOSTICA) and total protein is measured with a commercially available BCA assay (UPTIMA). The expression values are calculated as µg ovalbumin expression per mg of total protein. PrSSL denotes the promoter of SEQ ID NO: 1. Column 1: Pr7.5-filler-OVA+araC. Column 2: Pr7.5-filler-OVA. Column 3: Pr7.5-PrSSL-OVA+araC. Column 4: Pr7.5-PrSSL-OVA. Column 5: Pr7.5e-OVA+araC. Column 6: Pr7.5e-OVA. Column 7: Pr7.5e-PrSSL-OVA+araC. Column 8: Pr7.5e-PrSSL-OVA. Column 9: MVA-BN® (empty vector control)+araC. Column 10: MVA-BN® (empty vector control), without araC. The Y axis depicts µg ovalbumin expression per mg of total cell protein, with higher numbers representing more protein production, i.e. higher expression. Column 4 (Pr7.5-PrSSL-OVA) compared to column 2 (Pr7.5-filler-OVA), as well as column 8 (Pr7.5e-PrSSL-OVA) compared to column 6 (Pr7.5e-filler-OVA) show that PrSSL in combination with other promoters enhances expression of the reporter gene OVA. As in Example 3, the expression characteristics of PrSSL is late, since experimental addition of araC is abolishing the additive effect of PrSSL to the fused promoters. "Filler" indicates the random GC-rich sequence TTCAGTCCTATGG (SEQ ID NO: 6), which is intended to replace PrSSL as a control which occupies approximately the same space as PrSSLs in other constructs tested without conferring PrSSL's activity as a promoter.

In FIG. 2, the comparison of OVA protein expression using only the promoter Pr7.5 (Pr7.5-filler-OVA) is shown in columns 1 (with araC) and 2 (without araC). The significantly lower OVA expression evident in column 1 as compared to column 2 is due to inhibition of late promotion by Pr7.5 by araC. The higher OVA expression in column 4 (Pr7.5-PrSSL-OVA, without araC) than in column 2 (Pr7.5-filler-OVA, also without araC) indicates that the promoter PrSSL is capable of working in concert with other promoters to enhance the promotion to a level greater than that achievable with Pr7.5 alone. Further, the significantly lower OVA expression evident in column 3 (Pr7.5-PrSSL-OVA, with araC) as compared to column 4 (Pr7.5-PrSSL-OVA, without araC) is due to inhibition of late promotion by Pr7.5 and PrSSL by araC. Columns 5 and 6 (Pr7.5e-OVA with and without araC, respectively), indicate only a minimal reduction of OVA expression upon addition of araC, confirming the early nature of promotion by Pr7.5e. Columns 7 and 8 (Pr7.5e-PrSSL-OVA with and without araC, respectively) indicate a) that PrSSL can replace the missing late promoter element in Pr7.5e to yield good OVA expression (comparison of columns 6 and 8), and b) that addition of araC abrogates OVA expression down to approximately the same level as that obtained with Pr7.5e alone, both with and without araC (column 7 compared with columns 5 and 6). Empty vector control with and without araC treatment (columns 9 and 10) were used as reference for background OVA levels and set as zero (no expression).

Figure 3:
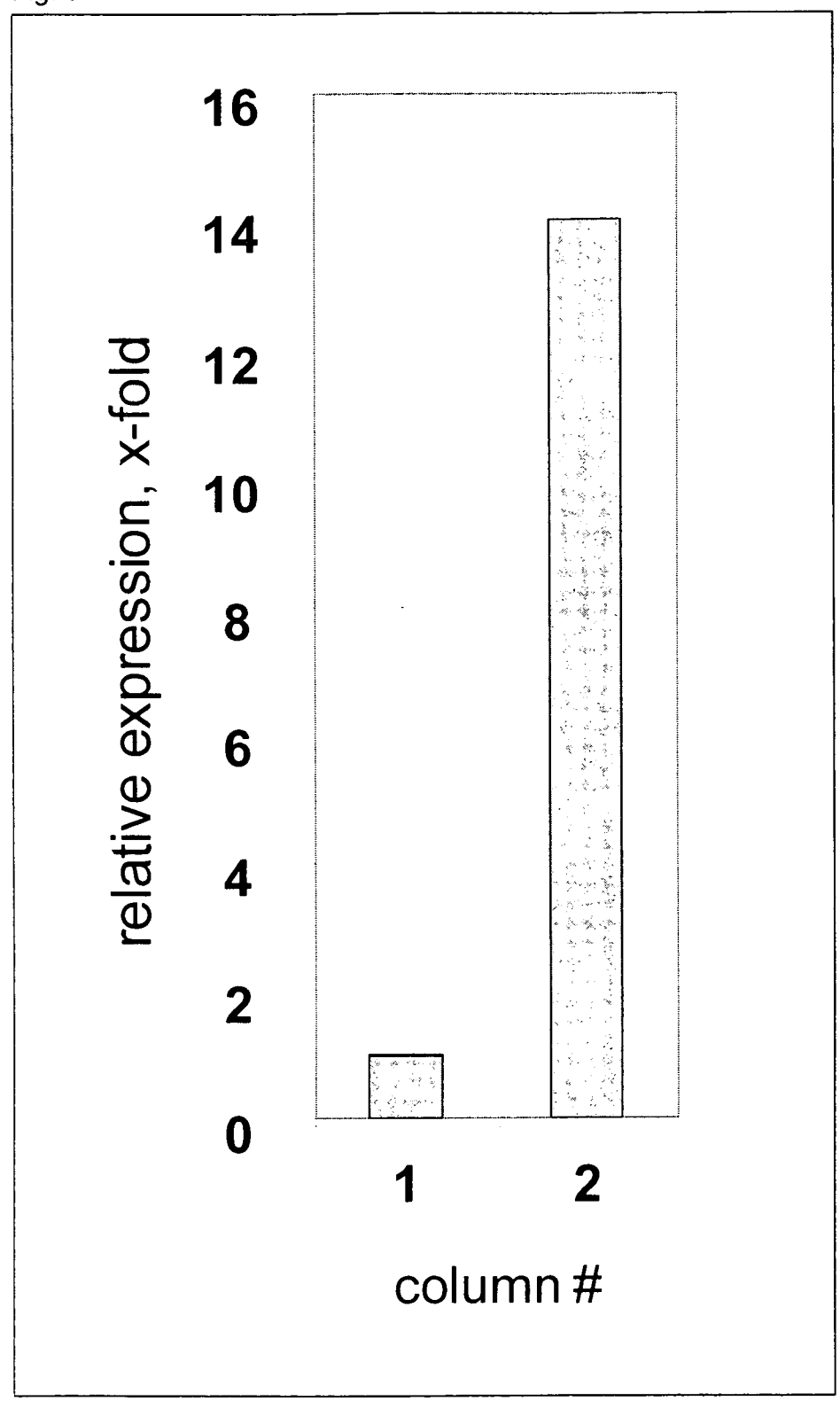
FIG. 3 Expression of the protein ovalbumin ("OVA") from recombinant MVA-BN® in the presence of PrATI, a well known strong late promoter from Cowpoxvirus in comparison to PrSSL. Expression is measured with a commercially available quantitative ovalbumin specific ELISA (SERAMUN DIAGNOSTICA) and total protein is measured with a commercially available BCA assay (UPTIMA). The value for expression is calculated as x-fold the expression of PrATI-filler-OVA (column 1). Column 1: PrATI-filler-OVA. Column 2: PrATI-PrSSL-OVA, where PrSSL corresponds to the promoter of SEQ ID NO: 1. The Y axis depicts x-fold ovalbumin expression, with higher numbers representing more protein production, i.e. higher expression. Fusion of the PrSSL sequence to the PrATI promoter results in 14-fold higher expression of ovalbumin as compared to that observed using PrATI alone, showing that PrSSL is a strong promoter in MVA.

A further experiment involving the well known PrATI late promoter of the ATI gene of cowpox virus shows the ability of PrSSL to work in tandem with a strong late class promoter. The results of this experiment are shown in FIG. 3, which shows the expression of OVA from recombinant MVA-BN® in the presence of PrATI (construct PrATI-filler-OVA), a well known strong late promoter from cowpox virus in comparison to the tandem PrATI-PrSSL-OVA. Expression is measured with a commercially available quantitative ovalbumin specific ELISA (SERAMUN DIAGNOSTICA) and total protein is measured with a commercially available BCA assay (UPTIMA). The value for expression is calculated as x-fold of the expression of PrATI-filler-OVA (column 1). As can be seen by comparing the relative protein levels in columns 1 and 2 of FIG. 3, fusion of the PrSSL sequence to the PrATI promoter (column 2, PrATI-PrSSL-OVA) results in 14-fold higher expression of ovalbumin. This demonstrates that PrSSL is a strong promoter in MVA and that it can cooperatively work in tandem with the PrATI promoter.

In total, then, the results shown in FIG. 2 and FIG. 3 confirm the ability of PrSSL to work in concert with other promoter elements. Coupled with an early-only promoter, PrSSL complements the early promoter activity with its own late promoter activity, resulting in significantly increased overall protein expression. Coupled with another early/late promoter, PrSSL enhances an already high protein expression level to an even higher level. Coupled with a poxviral late promoter, it strongly enhances the expression level.

TABLE 1

| nt position | -22 | -21 | -20 | -19 | -18 | -17 | -16 | -15 | -14 | -13 | -12 | -11 | -10 | -9 | -8 | -7 | -6 | -5 | -4 | -3 | -2 | -1 | +1 | +2 | +3 | +4 | +5 | +6 |
|---|---|---|---|---|---|---|---|---|---|---|---|---|---|---|---|---|---|---|---|---|---|---|---|---|---|---|---|---|
| ORF 1 | T | G | A | A | A | A | A | A | T | A | T | A | A | C | G | T | A | C | T | G | G | C | A | T | G | C | A | T |
| ORF 2 | A | T | A | A | A | C | T | A | T | G | A | G | T | T | A | T | C | T | T | A | T | T | A | T | G | T | T | T |
| ORF 3 | A | A | A | A | A | A | A | A | A | G | A | T | T | A | G | T | T | T | T | A | G | T | A | T | G | A | A | A |
| ORF 4 | T | A | A | T | T | T | T | T | G | T | G | T | T | C | T | A | T | T | A | A | T | C | A | T | G | G | G | T |
| ORF 5 | T | A | A | A | C | T | T | T | T | C | T | T | A | A | A | T | T | T | A | T | A | T | A | T | G | A | A | T |
| ORF 6 | T | T | A | A | A | T | A | A | A | A | A | G | A | T | A | A | A | C | A | T | A | A | A | T | G | G | A | T |
| ORF 7 | A | A | A | A | G | G | A | T | A | T | A | T | C | A | T | A | A | A | T | T | T | A | A | T | G | A | C | G |
| ORF 8 | T | A | G | T | T | A | T | A | A | T | T | T | A | G | A | T | T | A | T | T | T | A | A | T | G | G | G | T |
| ORF 9 | A | T | A | A | A | G | T | A | A | T | A | A | C | A | A | T | T | T | A | T | A | A | A | T | G | C | G | G |
| ORF 10 | G | C | A | A | T | A | T | A | A | T | T | A | A | A | A | A | T | T | A | A | A | A | A | T | G | A | T | T |
| ORF 11 | T | T | C | T | A | T | G | G | T | T | G | T | A | A | T | T | T | T | A | T | T | A | A | T | G | A | C | G |
| ORF 12 | C | C | T | A | A | A | T | A | A | A | A | A | A | A | A | T | T | T | T | A | T | A | A | T | G | T | T | G |
| ORF 13 | T | T | T | A | C | G | C | T | T | T | T | C | T | A | T | G | A | A | C | A | A | T | A | T | G | C | C | C |
| ORF 14 | C | C | T | A | T | G | T | A | T | T | T | T | A | A | C | T | T | A | A | A | T | A | A | T | G | G | A | G |
| ORF 15 | G | T | T | A | T | A | T | T | T | A | T | A | T | A | A | A | T | T | A | A | T | T | A | T | G | T | T | A |
| ORF 16 | C | T | A | A | A | A | A | T | T | T | T | T | T | T | A | A | C | T | T | A | A | T | A | T | G | C | C | A |
| ORF 17 | G | T | A | T | A | C | A | T | T | T | A | A | A | A | G | T | A | A | A | T | T | A | A | T | G | A | T | G |
| ORF 18 | C | A | G | T | A | G | T | A | A | T | T | A | T | A | T | T | A | T | A | T | A | A | A | T | G | A | A | T |
| ORF 19 | T | T | T | A | T | A | A | A | T | T | T | T | T | A | C | A | T | A | T | T | A | A | A | T | G | T | C | C |
| ORF 20 | A | A | A | G | G | A | T | T | G | A | A | T | T | A | T | A | C | A | C | T | A | A | A | T | G | C | C | A |
| ORF 21 | A | G | T | T | A | C | A | A | A | T | T | T | A | A | A | T | A | T | A | T | A | A | A | T | G | G | T | T |
| ORF 22 | A | G | A | G | A | T | T | T | T | T | T | T | T | C | G | T | C | A | T | T | T | A | A | T | G | T | A | G |
| ORF 23 | A | T | T | T | A | C | T | A | G | A | C | A | C | C | T | C | A | G | G | T | G | G | A | T | G | T | T | T |
| ORF 24 | G | T | T | T | C | T | A | A | A | A | A | C | T | G | T | A | C | T | A | A | A | A | A | T | G | G | A | C |
| most frequent nt at position | A | T | AT | A | A | T | A | A | T | T | T | T | T | A | A | A | A | T | A | T | T | A | A | T | G | G | A | T |
| frequency of occurence in % | 38 | 42 | 42 | 46 | 46 | 42 | 54 | 46 | 63 | 67 | 63 | 42 | 46 | 46 | 33 | 54 | 42 | 54 | 46 | 71 | 71 | 67 | 100 | 100 | 100 | 50 | 42 | 42 |
| second frequent nt at position | T | A |  | T | T | A | T | T | A | A | A | AG | A | T | T | T | C | T | T | A |  | A |  |  |  | A | T |  |
| frequency of occurence in % | 29 | 28 |  | 33 | 33 | 25 | 38 | 38 | 25 | 25 | 29 | 25 | 29 | 25 | 29 | 25 | 38 | 33 | 33 | 25 |  | 25 |  |  |  | 25 | 25 |  |

The invention claimed is:

1. A poxvirus expression vector comprising a promoter, wherein the promoter is operably linked to a heterologous nucleic acid encoding a protein, and wherein the promoter comprises the nucleotide sequence of SEQ ID NO:1 or a nucleotide sequence in which no more than 3 nucleotides have been substituted from the nucleic acid of SEQ ID NO:1.

2. The expression vector of claim 1, wherein the promoter comprises the nucleotide sequence of SEQ ID NO:1.

3. The expression vector of claim 1, wherein the promoter comprises the nucleotide sequence of SEQ ID NO:33.

4. The expression vector of claim 1, wherein the promoter comprises the nucleotide sequence of SEQ ID NO:34.

5. The expression vector of claim 1, wherein the promoter comprises the nucleotide sequence of SEQ ID NO:2.

6. The expression vector of claim 1, wherein the promoter comprises the nucleotide sequence of SEQ ID NO:3.

7. The expression vector of claim 1, wherein the promoter comprises the nucleotide sequence of SEQ ID NO:4.

8. The expression vector of claim 1, wherein the promoter comprises the nucleotide sequence of SEQ ID NO:5.

9. The vector of claim 1, wherein the promoter in the polynucleotide is joined directly to the start codon ATG of the heterologous nucleic acid encoding a protein.

10. The vector of claim 1, wherein the pox virus vector is a vaccinia virus vector.

11. The vector of claim 10, wherein the vaccinia virus vector is a modified vaccinia virus Ankara ("MVA") vector.

12. The vector of claim 11, wherein the MVA vector has the capability of reproductive replication in vitro in chicken embryo Fibroblasts ("CEF"), but no capability of reproductive replication in the human keratinocyte cell line HaCaT, the human embryo kidney cell line 293, the human bone osteosarcoma cell line 143B, and the human cervix adenocarcinoma cell line HeLa.

13. An isolated host cell comprising the vector of claim 1.
14. An isolated host cell comprising the vector of claim 2.
15. An isolated host cell comprising the vector of claim 3.
16. An isolated host cell comprising the vector of claim 4.
17. An isolated host cell comprising the vector of claim 5.
18. An isolated host cell comprising the vector of claim 6.
19. An isolated host cell comprising the vector of claim 7.
20. An isolated host cell comprising the vector of claim 8.
21. An isolated host cell comprising the vector of claim 9.
22. An isolated host cell comprising the vector of claim 10.
23. An isolated host cell comprising the vector of claim 11.
24. An isolated host cell comprising the vector of claim 12.

* * * * *